United States Patent [19]

Komis

[11] Patent Number: 4,553,968
[45] Date of Patent: Nov. 19, 1985

[54] EXTERNAL MALE URINARY CATHETER WITH GARMENT

[76] Inventor: Glenna Komis, P.O. Box 54033, Philadelphia, Pa. 19105

[21] Appl. No.: 492,145

[22] Filed: Jun. 9, 1983

[51] Int. Cl.[4] ............................................. A61F 5/44
[52] U.S. Cl. .................................. 604/349; 604/351; 604/353
[58] Field of Search ............................. 4/144.1–144.4; 604/346–353, 343, 345; 2/403, 405

[56] References Cited

U.S. PATENT DOCUMENTS

| | | | |
|---|---|---|---|
| 1,761,609 | 6/1930 | Becker | 604/350 |
| 2,445,694 | 7/1948 | Predmore | 128/295 |
| 2,494,477 | 1/1950 | Kurtz | 604/351 |
| 3,394,703 | 7/1968 | Orgel | 604/353 |
| 3,526,227 | 9/1970 | Appelbaum | 604/350 |
| 3,604,424 | 9/1971 | Windom | 128/295 |
| 3,661,156 | 5/1972 | McLaughlin | 604/349 |
| 3,721,243 | 3/1973 | Hesterman et al. | 604/353 |
| 4,073,295 | 2/1978 | Laufbahn | 604/353 |
| 4,270,539 | 6/1981 | Frosch | 4/144.3 |

FOREIGN PATENT DOCUMENTS

WO80/00535  4/1980  PCT Int'l Appl. .................. 604/349

OTHER PUBLICATIONS

"Bard-McGuire Urinal", Catalog of Bard Home Health Div., C. R. Bard Inc., Berkeley Heights, N.J. 07922, 1979.

Primary Examiner—C. Fred Rosenbaum
Assistant Examiner—J. L. Kruter

[57] ABSTRACT

An external male urinary catheter, generally in the form of a condom, connected at the lower portion to a collection receptacle by polyethylene drainage tubing and unified in a smooth and complete form at its upper portion and flange to the complementary tubular extension of a supporting garment by means of molding and meshing made possible by a vulcanization process.

7 Claims, 4 Drawing Figures

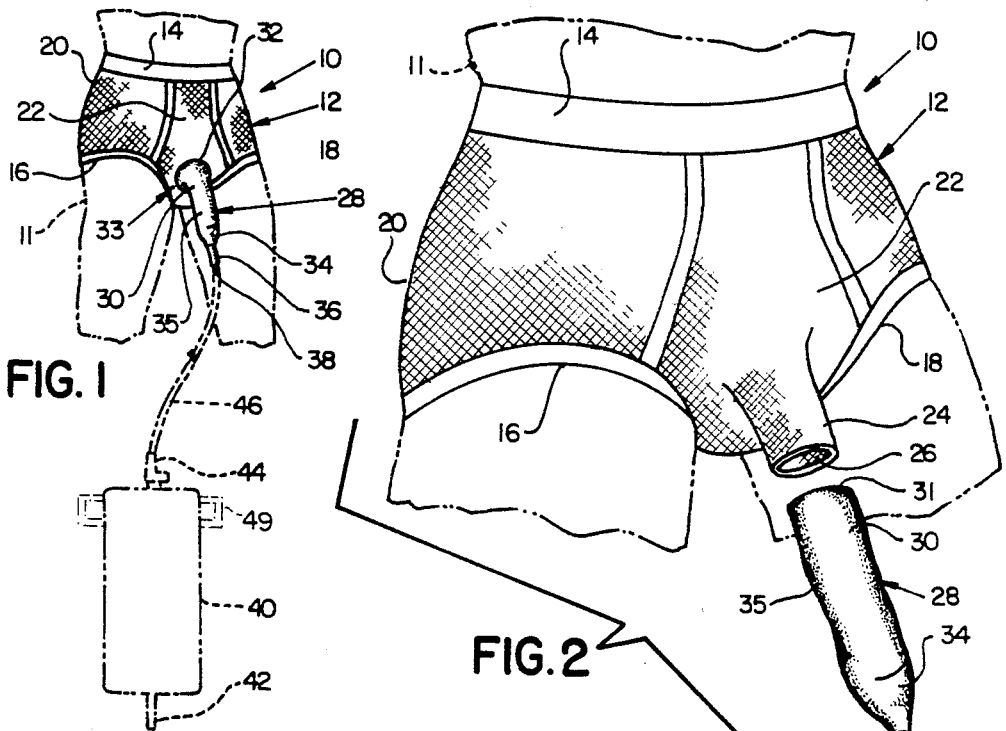
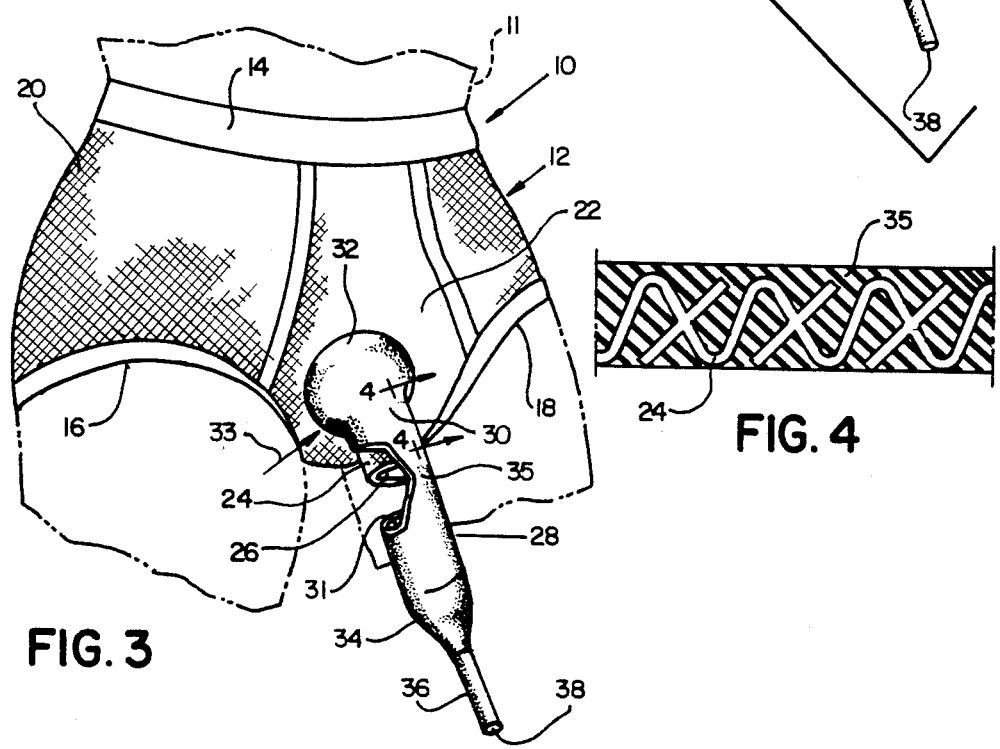

EXTERNAL MALE URINARY CATHETER WITH GARMENT

BACKGROUND OF THE INVENTION

1. Field of Invention

The present invention relates generally to a catheter and more specifically to an external male urinary catheter, generally in the form of a condom, connected at the lower portion to a collection receptacle by polyethylene drainage tubing and unified at the upper portion to a supporting garment by novel and unique means made possible by a vulcanization process among essential structures.

2. Description of the Prior Art

Traditional catheterization of the urinary bladder has involved the introduction of a catheter or tube through the urethra into the bladder for the purpose of withdrawing urine.

The hazards of introducing a catheter into the bladder are sepsis and trauma. The urinary bladder is normally a sterile cavity. However, microorganisms can enter the bladder by being pushed in during insertion of the catheter. In situations where the catheter is left in place over a long period of time, organisms can also move up the catheter lumen or the space between the catheter and the wall of the urethra. The omnipresent possibility of trauma is greater in the male patient, obviously because of the greater size of the male urethra.

Mostly in an effort to prevent the introduction of microorganisms into the urinary bladder and thereby avert the precipitation of a urinary tract infection, clinicians have resorted to the use of an external or exdwelling male urinary control device, basically a condom connected to a collection receptacle by drainage tubing. Exdwelling drainage is indicated particularly if a male patient is comatose or incontinent but still able to completely empty his bladder.

Unfortunately, such external male urinary control devices, as marketed today, in themselves present several problems. First, because of their construction, being fastened to the penis by adhesive tape, a hard rubber ring, sponge, or other tightly fitting mechanism, these devices may, over an extended period of time, constrict the blood vessels of the penis and significantly reduce the flow of blood to that organ. Loss of function and tissue necrosis and its complications, i.e., gangrene, can conceivably result. Second, the ability of the patient to completely empty his bladder becomes compromised and the purpose of catheterization defeated when a consequential obstruction to the flow of urine occurs by such constriction. In addition, urinary retention due to such obstruction may cause a reflux of urine back up the tract, predisposing the patient to kidney damage, infection, and pain.

Other less threatening side effects of the constricting mechanisms described above include pain and general discomfort. Moreover, because most patients with such an external catheter are elderly, confused, or severely debilitated males, the probability of their pulling off the device is greatly increased precisely because of the pain and discomfort imposed by the device itself.

An alternative method of external male urinary control involves a supporting garment attachment. Embodiments of such devices include: (1) a garment immediately receiving a collection receptacle with a valve mechanism, (2) a garment housing an inner waterproof lining tapered at the crotch and connected to tubing or a collection receptacle, (3) a garment attached by sewing to an extension of the upper portion of an external catheter, generally in the form of a condom, the catheter itself lined with bushing to enable a tight fit, and (4) a garment with a "snap-on" conical sheath embraced by a mechanical device which promotes the flow of urine by means of negative pressure.

Still other embodiments of external male urinary control devices include: (1) a belt supporting straps attached by buttons to an external catheter of the condom type connected at the opposite end to tubing and a collection receptacle, (2) a belt supporting the upper extension of an external catheter, generally in the form of a condom, with tubing and a collection receptacle, and (3) an external catheter, essentially a condom, itself contained within a collection receptacle.

Clearly, these embodiments represent devices which are partly or entirely cumbersome, uncomfortable, painful, and which may produce constriction of proximal blood vessels in the presence of certain features, i.e., bushing. Additionally, by virtue of their bulk and positioning or basic design, these devices have not proven to be effective in guiding and containing the gravitational flow of urine, thereby fostering conditions for leakage with consequent skin damage and odor, and creating embarrassment for the patient. Other disadvantages include difficulty in application and maintenance, and lack of adjustment to body size of the patient.

The present invention is directed to the improvement of external male urinary control by maintaining the desirable quality of an external catheter of the condom type, i.e., noninvasiveness, and, at the same time, removing the inherent disadvantages of the abovementioned devices.

SUMMARY OF THE INVENTION

Accordingly, the foremost object of the present invention is to remove any constricting mechanism, thereby greatly reducing or virtually eliminating the possibility of complications associated with such constriction, as described above. This object can be achieved by the novel design of the present invention which completely and smoothly unifies the lower portion of a supporting garment to the upper portion and flange of an external catheter, generally in the form of a condom, by means of molding and meshing made possible by a vulcanization process among essential structures.

A further object of this invention is to overcome the presence of any immediately surrounding bulk such as a urinary collection receptacle or drainage tubing, and to refine less sophisticated means of attachment, i.e., belts, snaps, valves, buttons, and bushing, thereby further promoting safety, comfort, reliability, and ease of application and maintenance.

Another object of this invention is to enhance functional integrity, durability, efficiency, reliability, and precision of external male urinary catheters of the condom type by means of the one-piece, molded construction enabled by the vulcanization process.

A further object of this invention is to provide flexibility within the overall design of the device, enabling adjustment to patient size in both garment and external catheter, i.e., small-medium-large, to further enhance precision, efficiency, and reliability.

Still another object of this invention is to enable easy application and maintenance by both health care professionals and laypersons by means of integration of simple but optimal features.

Still another object of this invention is to provide a disposable, 100% cotton or cotton blend undergarment of the men's brief type ordinarily worn by men to encourage absorption, ventilation, and evaporation of bodily fluids, thereby preserving integrity of the skin and preventing rash, breakdown, and infection.

Still another object of this invention is to decrease the possibility of the development of unpleasant odor due to leakage by means of the more secure, more precise, virtually moisture-proof construction made possible by the vulcanization process between the garment and the external catheter.

Finally, an object of this invention is to enhance the self-esteem of both bedridden and ambulatory patients by providing a safer, more comfortable, more reliable means to cope with urinary incontinence.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view of the present invention, illustrating the method of applied utilization, with the external catheter and garment in unison.

FIG. 2 is an exploded perspective view, describing the association between the garment and the external catheter.

FIG. 3 is an assembled perspective view, with a part broken away to show the degree to which tubular member 24 extends into aperture 31 of external catheter 28.

FIG. 4 is an enlarged view of a section taken along Line 4—4, emphasizing the embedding of rubber within strands of cotton to produce a meshing which is complete and smooth.

DESCRIPTION OF THE PREFERRED EMBODIMENTS

Now, with specific reference to the drawings, an embodiment of the present invention is generally designated by reference numeral 10, such embodiment enshrouding the body 11 of a male wearer.

The integral features of this invention, as shown in FIG. 1, include a garment 12 attached to a rubber external catheter 28, generally in the form of a condom, by a vulcanization process rendering garment 12 and external catheter 28 a smooth, continuous whole. External catheter 28 is connected to collection receptacle 40 by means of polyethylene drainage tubing 46.

With reference to FIG. 2, garment 12 represents 100% cotton or cotton blend underwear of the "jockey" short type, with elasticized right and left leg openings 16 and 18, respectively, and with an elasticized waistband 14 at the top, supporting a rear panel 20 and a front panel 22. It is understood that flexibility within the overall design of this invention is maintained to enable adjustment to patient size in both garment and external catheter, i.e., small-medium-large.

Still with reference to FIG. 2, an integral structure of garment 12 is a wave cotton or cotton blend extension of front panel 22 which continues in cylindrical form to shape a tubular member 24, and ends to create an aperture 26. Aperture 26 has no rim or otherwise conspicuous, palpable ending.

To tubular member 24 is attached in a complementary fit the upper portion 30 and flange 32 of external catheter 28. FIG. 3 shows the degree to which tubular member 24 extends into aperture 31 of external catheter 28. External catheter 28, generally in the form of a condom, is comprised of rubber treated by the appropriate industrial process(es), i.e., vulcanization, rendering such rubber a thin, flexible, resilient sheath capable of being molded, meshed, and attached at its upper portion 30 and flange 32 to tubular member 24. Such attachment terminates at a point indicated by Arrow 33. FIG. 4 emphasizes the embedding of rubber 35 within strands of woven cotton 24 to produce the said meshing which is complete and smooth.

With reference back to FIG. 2, between upper portion 30 and lower portion 34 of external catheter 28 is body 35 which is essentially the continuous sheath of treated rubber.

The lower portion 34 of external catheter 28 is thickened or reinforced by the appropriate industrial process(es) so as to bear a contoured tubular member 36 with an opening 38.

As illustrated in FIG. 1, collection receptacle 40 is attached to polyethylene drainage tubing 46 at opening 44 and further connected to contoured tubular member 36 at its opening 38. Polyethylene drainage tubing 46 may be taped to the male patient's thigh to prevent dangling and subsequent pain and discomfort. Urinary collection receptacle 40, basically a polyethylene bag, has means 49 to enable it to be attached to the ambulatory patient at his calf by Velcro straps or to the bedside of the bedridden patient at a level below the bladder to assure drainage by gravity and thereby prevent reflux of urine. Urine accumulated within collection receptacle 40 can be removed by means of a valvular member 42 at the bottom of said receptacle.

I claim:

1. An external male urinary catheter assembly comprising a thin, flexible, resilient tubular catheter dimensioned to be positioned in enclosing relation to a substantial portion of the penis, said catheter including a reinforced end portion forming a contoured, open-ended tubular member, drainage tubing communicating at one end with said tubular member and extending to a connection element, said element being in fluid communication with a collection receptacle having means for attachment either to the ambulatory wearer at his calf or to the bedside of the bedridden wearer; said catheter being smoothly and completely united among essential structures, the end of said catheter opposite to said reinforced end portion forming a circular flange; and a supporting garment of the men's brief type, said garment composed of strands of an absorbent material and having a complementary annular outwardly projecting tubular portion on the front thereof, said flanged end portion comprising a vulcanized rubber material engaging said annular portion and integrally united thereto, the rubber material of said flanged end portion being embedded within said strands so as to provide a continuous smooth meshing of the strands of absorbent material and the rubber material.

2. A catheter as described in claim 1 that is disposable after expiration of optimal utility, wherein said garment material is disposable.

3. A catheter as desribed in claim 1 wherein said garment is comprised of cotton material.

4. A catheter assembly as described in claim 1 wherein said tubular catheter member between said flange and said reinforced end portion is in the nature of a condom so as to snugly engage the penis without constricting the same.

5. A catheter assembly as described in claim 4 wherein the tubular extension comprises a woven fabric and said entire tubular catheter member is of vulcanized rubber material, said flange portion being embedded within said woven fabric.

6. A catheter as described in claim 1 wherein said garment has fabric front and rear panels with an elasticized waist band and elasticized leg openings, said tubular portion being formed in said front panel to register with the penis.

7. An external urinary catheter for use by male patients in assembly with drainage tubing extending to a collection receptacle adapted to be attached to an ambulatory wearer at his calf or to the bedside of the bedridden wearer, said catheter comprising a supporting garment of ventilated, absorbent material having a plurality of strands having front and rear panels connected together to snugly encircle the trunk of the male patient, said garment having an elasticized waist band and elasticized leg openings to retain the garment in place, the front panel having a frontal opening and an annular outwardly projecting portion surrounding the frontal opening, said portion having a diameter adapted to encircle the penis of the male patient without constricting the same; said catheter further comprising a thin, flexible, resilient tubular member, generally in the form of a condom, dimensioned to fit in enclosing relation to a substantial portion of the penis, the diameter and resilience of said tubular member snugly engaging the penis without constricting the same, said member having a base portion at one end engaging said annular portion and securely united therewith, said member including a reinforced portion remote from said base portion adapted to be positioned beyond the end of the penis and having a contoured, open-ended tubular member for connection to said tubing, said tubular entity being composed of a vulcanized rubber material, and connected to said annular projecting portion by the rubber material which penetrates the absorbent material of the and integrally unites the member to said annular projecting portion to provide a smooth meshing of the strands of absorbent material and the rubber material.

* * * * *

UNITED STATES PATENT AND TRADEMARK OFFICE
CERTIFICATE OF CORRECTION

PATENT NO. : 4,553,968

DATED : November 19, 1985

INVENTOR(S) : Glenna Komis

It is certified that error appears in the above-identified patent and that said Letters Patent is hereby corrected as shown below:

```
Column 3, line 56, "jockey short" should read --men's brief--;
          line 64, "wave" should read --woven--.
Column 5, line 20, after "strands" insert --, said garment--.
Column 6, line 16, delete "entity" and insert --member--;
          line 19, after "of the" insert --garment--.
```

Signed and Sealed this

Sixth Day of May 1986

[SEAL]

*Attest:*

DONALD J. QUIGG

*Attesting Officer*  *Commissioner of Patents and Trademarks*